United States Patent
Göhring et al.

(10) Patent No.: US 8,551,761 B2
(45) Date of Patent: Oct. 8, 2013

(54) CARTRIDGE AND DEVICE FOR ANALYZING BIOLOGICAL SAMPLES USING TEMPERATURE-CONTROLLED BIOLOGICAL REACTIONS

(75) Inventors: Jens Göhring, Erfurt (DE); Stefan Heydenhauss, Erfurt (DE); Friedrich Menges, Jena (DE); Reiner Spolaczyk, Hamburg (DE); Jana Lepschi, Jena (DE)

(73) Assignee: Zenteris GmbH, Jena (DE)

( * ) Notice: Subject to any disclaimer, the term of this patent is extended or adjusted under 35 U.S.C. 154(b) by 0 days.

(21) Appl. No.: 13/127,240

(22) PCT Filed: Oct. 24, 2009

(86) PCT No.: PCT/EP2009/007622
§ 371 (c)(1),
(2), (4) Date: Sep. 7, 2011

(87) PCT Pub. No.: WO2010/060509
PCT Pub. Date: Jun. 3, 2010

(65) Prior Publication Data
US 2011/0312535 A1    Dec. 22, 2011

(30) Foreign Application Priority Data
Nov. 3, 2008    (DE) .......................... 10 2008 054313

(51) Int. Cl.
| | |
|---|---|
| C12M 1/00 | (2006.01) |
| C12M 1/36 | (2006.01) |
| C12M 1/38 | (2006.01) |
| C12M 1/34 | (2006.01) |
| C12M 3/00 | (2006.01) |
| G01N 15/06 | (2006.01) |
| G01N 35/00 | (2006.01) |
| G01N 33/44 | (2006.01) |

(52) U.S. Cl.
USPC .................. 435/283.1; 435/286.5; 435/287.1; 435/287.2; 422/68.1; 436/43; 436/94

(58) Field of Classification Search
USPC ..................... 435/283.1, 286.5, 287.1, 287.2; 422/68.1; 436/43, 94
See application file for complete search history.

(56) References Cited

U.S. PATENT DOCUMENTS

| | | | |
|---|---|---|---|
| 5,229,297 A | * | 7/1993 | Schnipelsky et al. ........... 436/94 |
| 6,613,286 B2 | | 9/2003 | Braun, Sr. et al. |
| 7,011,794 B2 | | 3/2006 | Kagan et al. |

(Continued)

FOREIGN PATENT DOCUMENTS

DE    WO2008/000770    *    1/2008

*Primary Examiner* — Narayan Bhat
(74) *Attorney, Agent, or Firm* — Rankin, Hill & Clark LLP

(57) ABSTRACT

The cartridge according to the invention for analysing biological samples comprises:
a reaction chamber and a biochip mounted in the reaction chamber,
a filling nozzle connected so as to communicate with the reaction chamber, and
a compensation chamber connected so as to communicate with the reaction chamber, wherein the reaction chamber, the compensation chamber and all lines connected thereto form a chamber sealed as far as the filling nozzle, wherein
the filling nozzle forms a free passage to the reaction chamber from outside the cartridge, and a stopper is provided which fits positively and tightly in the filling nozzle in such a way that, when pressed in over a certain distance, fluid is displaced from the filling nozzle towards the reaction chamber.

12 Claims, 10 Drawing Sheets

(56) References Cited

U.S. PATENT DOCUMENTS

Figure 1:
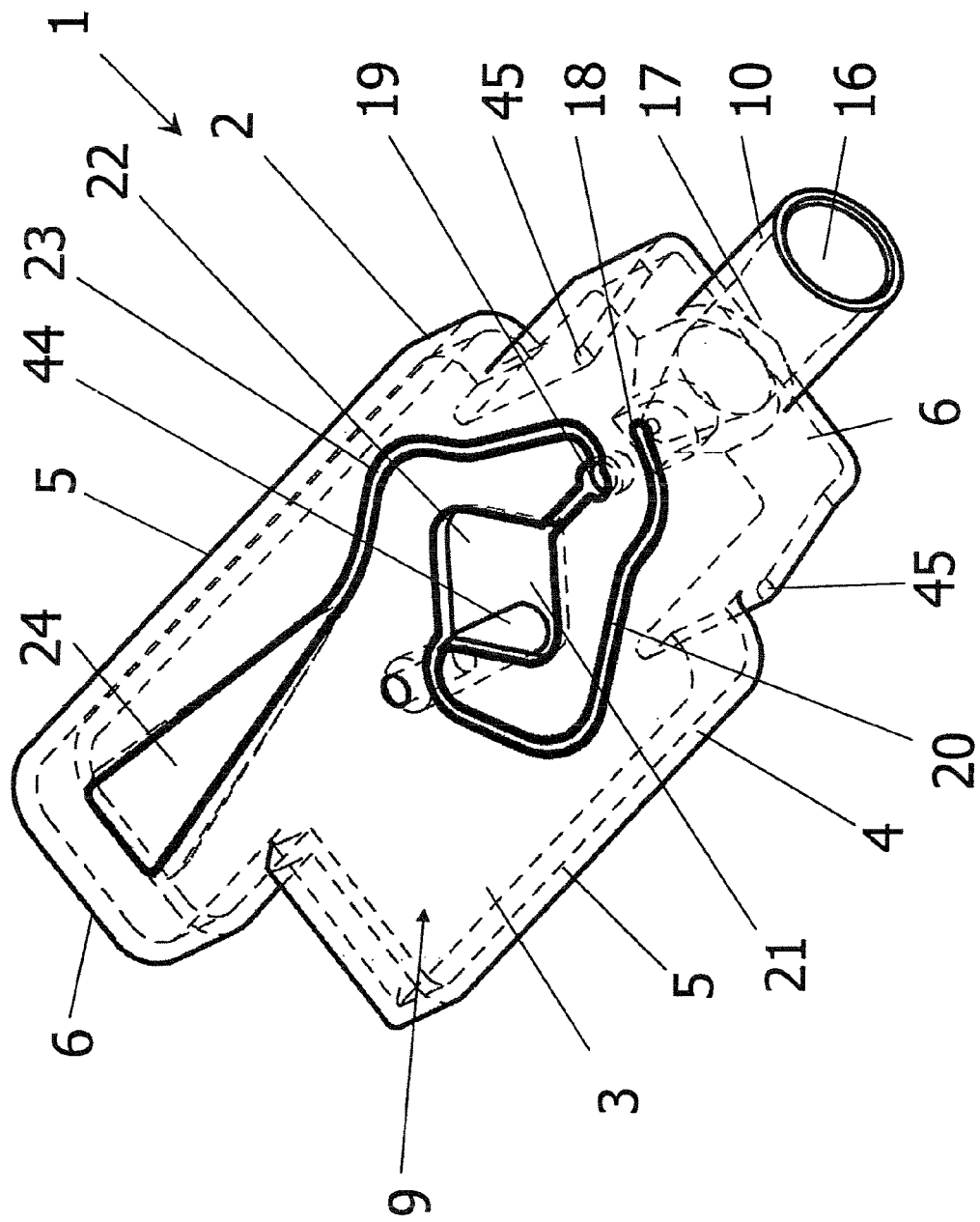

| | | |
|---|---|---|
| 7,863,035 B2 | 1/2011 | Clemens et al. |
| 2002/0064482 A1* | 5/2002 | Tisone et al. ................ 422/100 |
| 2007/0154922 A1 | 7/2007 | Collier et al. |
| 2009/0197778 A1* | 8/2009 | Lepschi et al. ................ 506/32 |
| 2010/0068822 A1 | 3/2010 | Heydenhauss et al. |
| 2010/0105130 A1 | 4/2010 | Hanafusa et al. |
| 2010/0291588 A1 | 11/2010 | McDevitt et al. |

* cited by examiner

CARTRIDGE AND DEVICE FOR ANALYZING BIOLOGICAL SAMPLES USING TEMPERATURE-CONTROLLED BIOLOGICAL REACTIONS

The invention relates to a cartridge and an apparatus for analysing biological samples using temperature-controlled biological reactions.

A biochip has a generally flat substrate with different catcher molecules located at predetermined points, the spots, on the surface of the substrate. A sample substance provided with a marking reacts with certain catcher molecules on the lock and key principle. The catcher molecules are generally comprised of DNA sequences (see e.g. B. EP 373 203 B1) or proteins. Such biochips are also known as arrays or DNA arrays. The markings are often fluorescent markers. The fluorescence intensity of the individual spots is determined by an optical reader. This intensity correlates with the number of marked sample molecules immobilised by the catcher molecules.

WO 2005/108604 A2 discloses a heatable reaction chamber for processing a biochip. This reaction chamber has an elastic membrane. Mounted on the membrane is a silicon biochip. Provided as heating device is a nickel-chromium thin-film conductor path. Such nickel-chromium thin-film conductor paths have high electrical resistance and a correspondingly high heat output. In addition to the conductor path for the resistance heating, a further conductor path is provided for temperature measurement.

In this known reaction chamber, one housing wall is designed as membrane, so that the biochip may be pressed against a cover glass lying opposite the membrane by means of a stopper. By this means, a reaction fluid in the reaction chamber is displaced from the surface of the biochips and does not disturb the optical detection. A seal is provided between the membrane and the cover glass. The sample fluid is poured in by means of a filling cannula, which is pushed through the seal. In connection with stoppers, surplus sample fluid is drawn out of the reaction chamber by means of a pressure equalisation cannula.

In U.S. Pat. No. 5,759,846 and U.S. Pat. No. 6,130,056 a reaction chamber for holding biological tissues is described in each case. The reaction chamber contains a flexible circuit board with electrodes. By pressing together the tissue and the flexible circuit board, an electrical contact can be made between the biological tissue and the electrodes of the flexible circuit board, so that an electrical pickup may be made directly at the biological tissue.

Described in DE 10 2005 09 295 A1 is a chemical reaction cartridge with several chambers. By rolling a roller over the surface of the cartridge, fluids may be moved from one chamber to another. Also provided is a metal bar which may be used to exert pressure, vibration, heat, coldness or the like on the cartridge, in order to accelerate the chemical reaction in the cartridge.

From K. Shen et al. Sensors and Actuators B 105 (2005), pages 251-258, "A microchip-based PCR device using flexible printed circuit technology", the use is known of a flexible circuit board for the heating of a reaction chamber, which is provided for a PCR process. The reaction chamber comprises a glass plate, a frame and a plastic cover. On the inside of the glass plate the flexible circuit board is fixed either directly by means of an adhesive bond or by means of a copper chip lying in between. On account of the good thermal properties of the flexible circuit board, heating rates of 8° C./s have been obtained. Formed on the flexible circuit board is a conductor path which is used both for heating and also for temperature measurement. The heating takes place during a "heating state" and the measurement during a "sensing state", with these states being offset in time.

Described in WO 2007/051863 A2 is a reaction chamber, in which a biochip may be processed. The reaction chamber has two opposite walls, between which the biochip is located. One of the two walls is transparent, which is effective both for the exciting radiation and for the signals emitted by the biochip. At least one of the two walls is so movable that the space between the biochip and the transparent wall may be compressed, by which means the sample solution between them may be displaced.

US 2004/0047769 A1 and JP 2002-365299 A respectively disclose a pocket of plastic material used to hold blood. The blood may be treated for analysis using a DNA array. The DNA array is integrated in the pocket. By means of rollers, the blood and a sample solution in the pocket are displaced towards the DNA array and a waste products area behind it. The DNA array may be read in a conventional manner.

After the blood has once been put in this bag, the aim is for all reactions to take place in the bag, without the blood and the solutions it contains leaving the bag and coming into contact with the environment. In this way it is possible to avoid contamination by blood which may be infected.

U.S. Pat. No. 6,569,674 B1 describes an apparatus for the conduct of biological reactions. A reaction chamber has a microscope glass slide which is covered by a flexible film. Formed in the glass slide are first and second passages which lead into the reaction chamber between the substrate and the flexible film. The flexible film is fastened to the substrate by an adhesive. Also defined in this patent is a sample treatment chip which is in contact with the substrate and in turn has an opening, designed for opening the substrate. The film may be subjected to pressure from a roller.

Described in International Patent Application PCT/EP2007/010298, not yet published, is an apparatus for the analysis of biological samples using temperature-controlled biological reactions. This comprises a reaction chamber to accommodate a biochip. The reaction chamber has at least one transparent window, so that exciting light from outside may be radiated on to the biochip and fluorescent light from the biochip may be emitted outwards to a measuring device. A membrane forming at least one wall of the reaction chamber is provided and is made elastic, so that the window and the biochip may be pressed against one another in order to displace sample solution lying between them. Provided in a filling hole is a non-return valve through which the sample material may be fed to the reaction chamber.

With this apparatus it is a drawback that, in filling, a relatively precisely measured sample volume must be fed into the cartridge to create the desired pressure. This requires a so-called "positive displacement pipette", which is in a position to build up the necessary overpressure for the non-return valve. After the removal of the pipette there is always, as a matter of principle, a residue of the sample ahead of the non-return valve, which may lead to contamination. The structure of this apparatus is relatively complex.

WO 02/50535 A1 discloses a cartridge for the analysis of biological samples, in particular blood samples. This cartridge has fluid holding chambers, each of which may be supplied with fluid via a common inlet, through a branching line system. The inlet is designed so that a syringe may be plugged into it. The fluid holding chambers are each connected to an air vent/fluid stopper, through which the air present in the fluid holding chambers before filling may escape.

DE 100 13 242 A1 discloses a chemical analyser with an analysis cassette. The analysis cassette is made up of a bottom substrate and a top substrate, with reaction cells formed between the two substrates. Formed on the top substrate is a guide orifice for connecting to an injector. Also provided are air vents for connection with fine orifices, each suitably connected to end sections of fine flow passages for the removal of air contained in them.

Described In DE 102 44 154 A1 is a carrier element for diagnostic tests, in particular to determine agglutination. This carrier element has a bottom part and a top part. There is a central inlet, from which at least two feed passages lead in each case to a reaction chamber. From each reaction chamber a vent passage branches to the outside, preventing any back-pressure on injection of the fluid. The air present in the reaction chambers is able to escape to the outside.

DE 295 00 587 U1 discloses a kit for blood group determination, which has a passage system with several passages. Provided at the end of each passage is a camera, described as the antibody compartment. The individual passages converge at a passage system distributor, which merges into a syringe holder. In each of the passages are valves which form a kind of non-return valve, intended to prevent any return flow of injected material. The antibody compartments are sealed at least on one side by a flexible film, and are provided on the other side with an optical lens.

Known from DE 10 2004 023 217 A1 is a reaction module which has a rigid plate-like support with a flexible body mounted on top. Passages and chambers are formed between the two bodies. The solution is injected using a syringe. The needle of the syringe is injected directly into the flexible body. Such a module is designed to be sealed and may be disposed of, so that it can be used to hold dangerous solutions. This module is intended for use, amongst other things, for the detection or identification of biopolymers such as DNA or RNA using a hybridisation unit.

The invention is based on the problem of creating a cartridge for the analysis of biological samples using temperature-controlled biological reactions, which is easy to fill so that there is no risk of contamination from escaping sample solution and in addition the most ideal reaction conditions are provided in the reaction chamber.

The problem is solved by a cartridge with the features of claim 1. Advantageous developments are set out in the dependent claims.

The cartridge according to the invention for analysing biological samples comprises:
  a reaction chamber and a biochip mounted in the reaction chamber,
  a filling nozzle connected so as to communicate with the reaction chamber, and
  a compensation chamber connected so as to communicate with the reaction chamber, wherein the reaction chamber, the compensation chamber and all lines connected thereto form a chamber sealed as far as the filling nozzle, wherein
the filling nozzle forms a free passage to the reaction chamber from outside the cartridge, and a stopper is provided which fits positively and tightly in the filling nozzle in such a way that, when pressed in over a certain distance, fluid is displaced from the filling nozzle towards the reaction chamber.

By this means, the following advantages are obtained:
1. Since the filling nozzle is open, the sample solution may be introduced easily, e.g. using a standard pipette. There is no need for a syringe, to pierce a membrane. No pressure must be built up in order to penetrate a valve. In filling, no force or counterforce needs to be overcome for the sample to be inserted in the cartridge. Filling is therefore effected without pressure. There is no danger that part of the sample will be spilt during filling.
2. The sample solution is put under pressure when the stopper is pressed in. This increases the boiling point. As a result, even under heating to temperatures in the range of around 100° C., no gas bubbles occur in the sample solution, which might impair measurements.
3. The air in the compensation chamber acts on the sample solution like an elastic spring element, allowing further displacement of the sample solution, while the restoring force exerted on the sample solution by the air is small. Consequently, the force which must be applied to a transparent flexible film, bounding one side of the reaction chamber, in order to displace the sample solution, is also small in comparison with conventional reaction chambers with membranes.
4. This restoring force makes the process of displacing the fluorescing sample solution reversible, if the force applied to the film is varied. This makes possible real-time PCR and the measurement of a melting curve.
5. The tight closing of the cartridge by the stopper rules out any risk of contamination of the environment.

The open filling nozzle is connected via lines communicating with the reaction chamber, a filling level indicator and the compensation chamber, so that before filling, the respective normal pressure prevails in all hollow spaces of the cartridge. On filling with the sample fluid, the filling nozzle fills up. The air in the cartridge is compressed by the pressing in of the stopper. Since the sample chamber, the compensation chamber and the filling nozzle are in communication with one another, the pressure in the overall container system is equalised simultaneously. Here the volumes are so dimensioned that the reaction chamber is completely filled with sample fluid, and an internal overpressure of 0.3-0.5 bar and preferably around 0.4 bar is generated.

The apparatus has an open filling nozzle. This makes it possible to introduce the sample solution using a pipette. It is not necessary to use a cannula with which, as with conventional apparatus of this kind, a seal is pierced, or to press the sample fluid through a valve under pressure.

In one embodiment of the apparatus according to the invention, the area of the cartridge opposite the biochip is in the form of a transparent film. The flexible transparent film serves as a window for optical measurements of the sample solution. In this variant it is advantageous that the biochip itself need not be moved in the reaction chamber.

In one embodiment of the present invention, one side of the reaction chamber is bounded by a circuit board. The biochip is mounted directly on the circuit board. Heating/measuring structures may be integrated in this circuit board. Such a circuit board serves for heating and measurement of the sample solution.

Provided in the cartridge is a filling line section, which extends from the filling nozzle around the reaction chamber and leads into a boundary zone of the reaction chamber at a distance from the filling nozzle.

The cartridge is filled with the open filling nozzle facing upwards. The stopper is pressed into the filling nozzle, so that the sample fluid is driven into the reaction chamber, which is filled from the bottom to the top. By this means, air is displaced from the reaction chamber into a compensation chamber downstream of the reaction chamber. This has the advantage that the air from the reaction chamber is completely displaced into the compensation chamber.

For scanning, the cartridge according to the invention is arranged in an apparatus for the analysis of biological samples with the filling nozzle facing downwards. In conducting an optical scan of the reaction chamber, a pressure of preferably 1 bar to 4 bar is created in the scanning chamber in such a way that the film fits up against the biochip and the sample fluid is displaced from the reaction chamber in the direction of the compensation chamber, while an air bubble remains above the sample fluid in the compensation chamber.

In the case of the apparatus for analysing biological samples, in the procedural steps in which no optical scanning takes place and the reaction chamber is heated, a pressure is created in one scanning chamber of the apparatus which corresponds roughly to the internal pressure in the reaction chamber.

The cartridge is made preferably of polypropylene (PP). This is an inert plastic material which requires no additional passivation of surfaces in order in order to make possible temperature-controlled biological reactions (in particular the PCR process) in the reaction chamber. The cartridge may however also be made of another suitable plastic such as e.g. cycloolefincopolymer (COC) or another suitable material.

The transparent plastic film may be provided on its side facing the biochip with an adhesive or bonding layer which can be activated when it comes into contact with the sample solution. When the plastic film is pressed on to the biochip it adheres to the biochip, thereby preventing sample solution from entering between the biochip and plastic film. This adhesive or bonding layer is preferably provided on that area of the film which is not in contact with the area of the biochip containing its spots. The adhesive or bonding layer is thus provided so as to run around the active area of the biochip.

The invention will be explained with the aid of an embodiment illustrated in the drawings. The drawings show in schematic form in:

FIG. 1 a perspective view of a casing of a cartridge according to the invention

Figure 2:
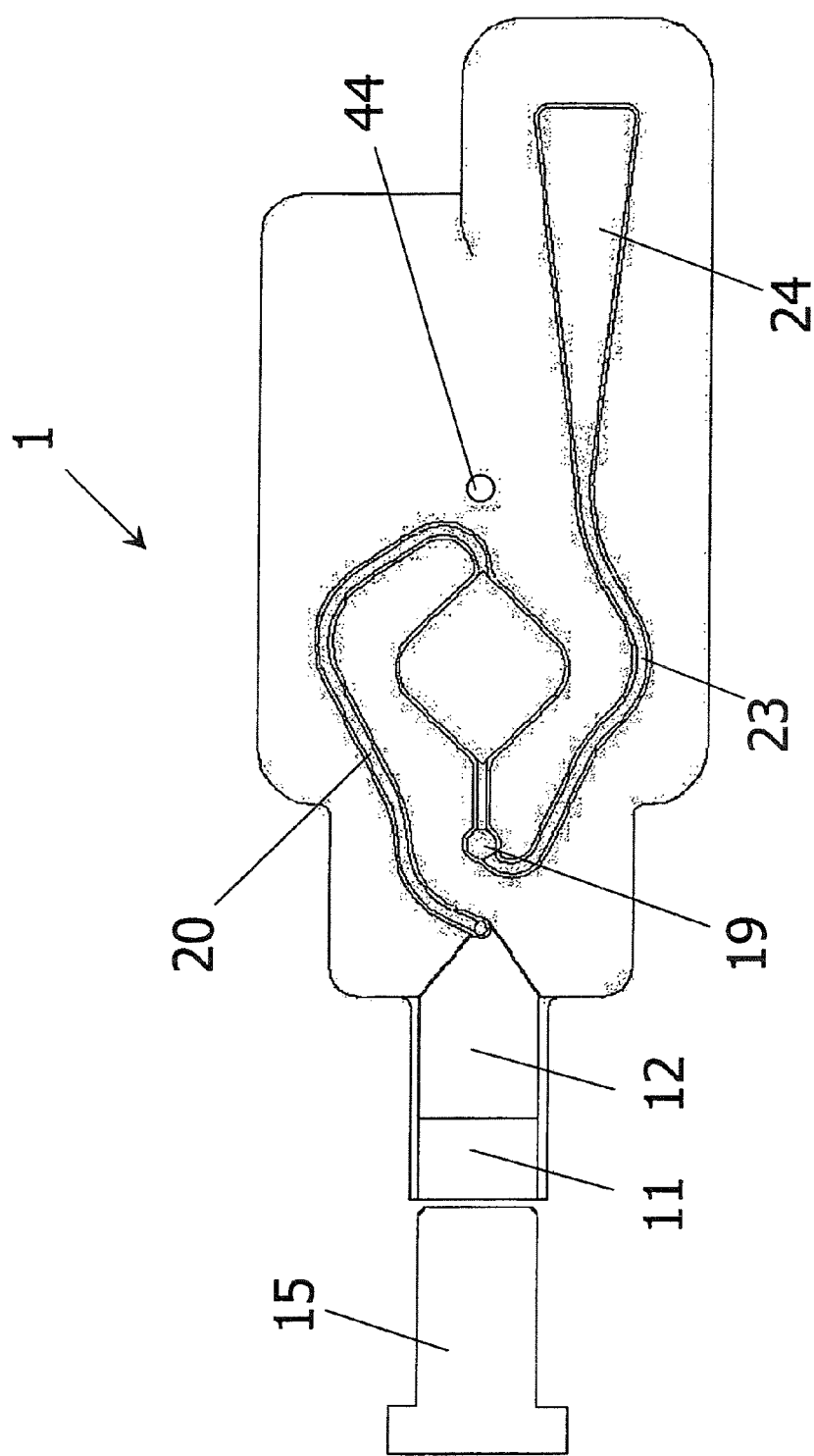
Figure 3:
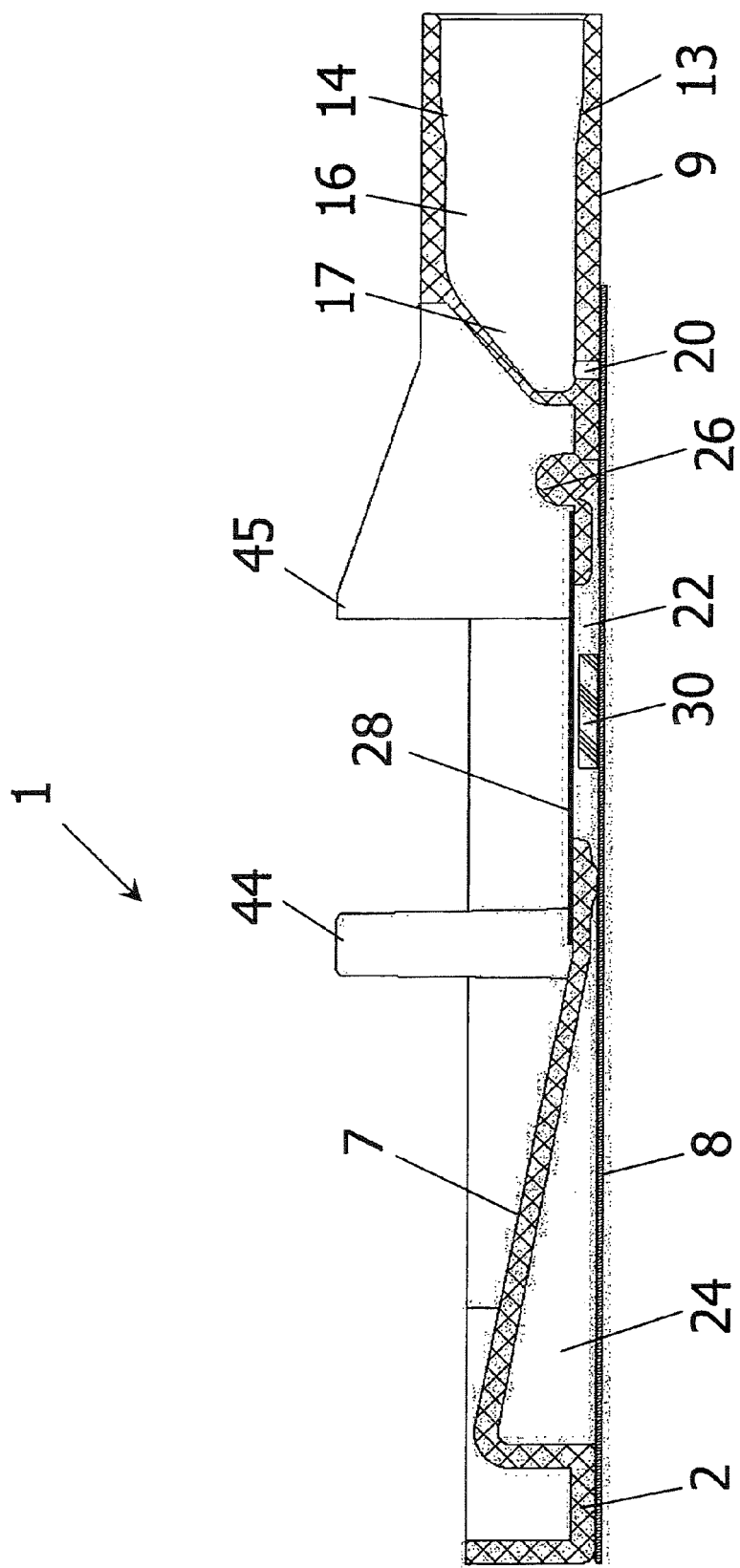
Figure 4:
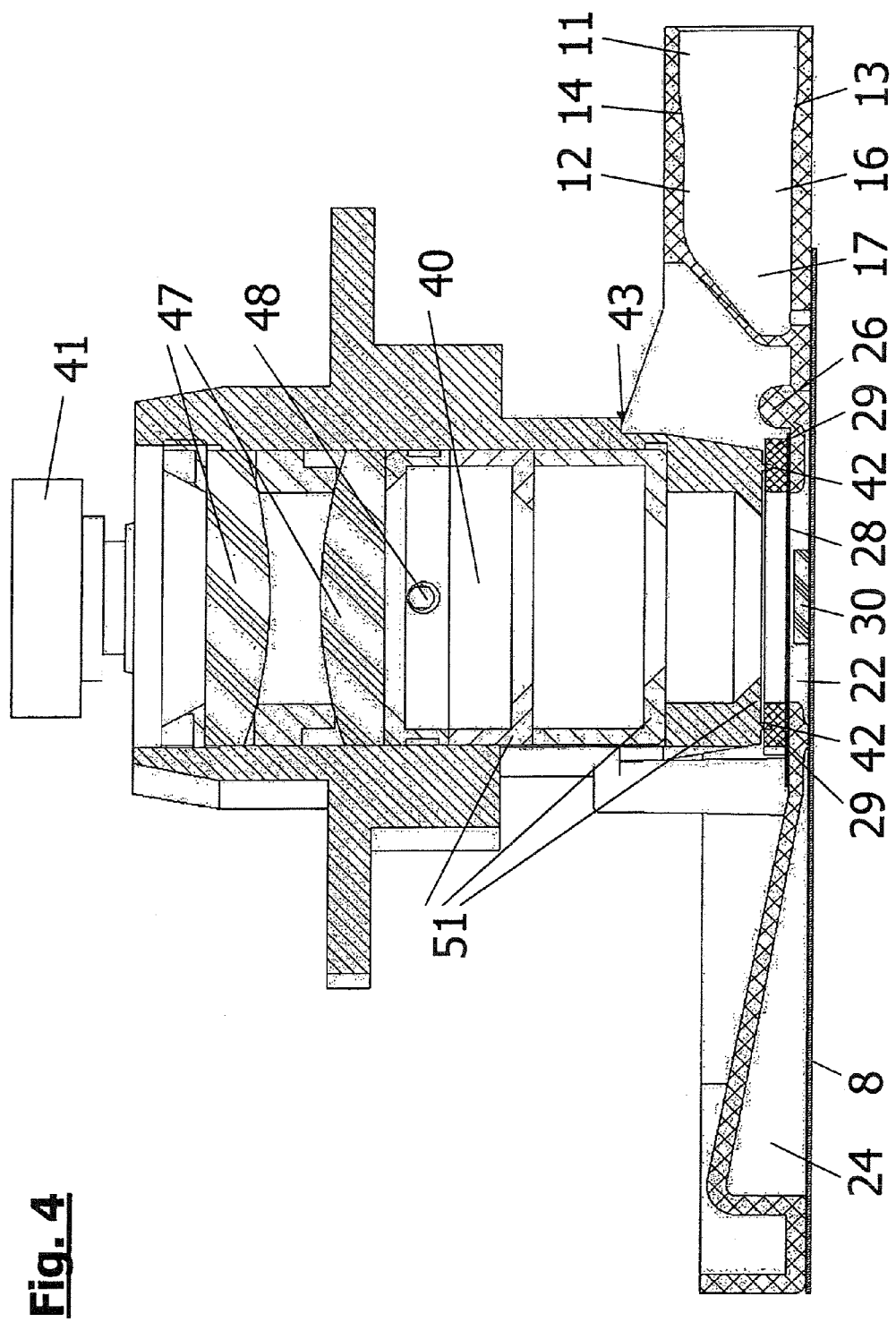
Figure 5:
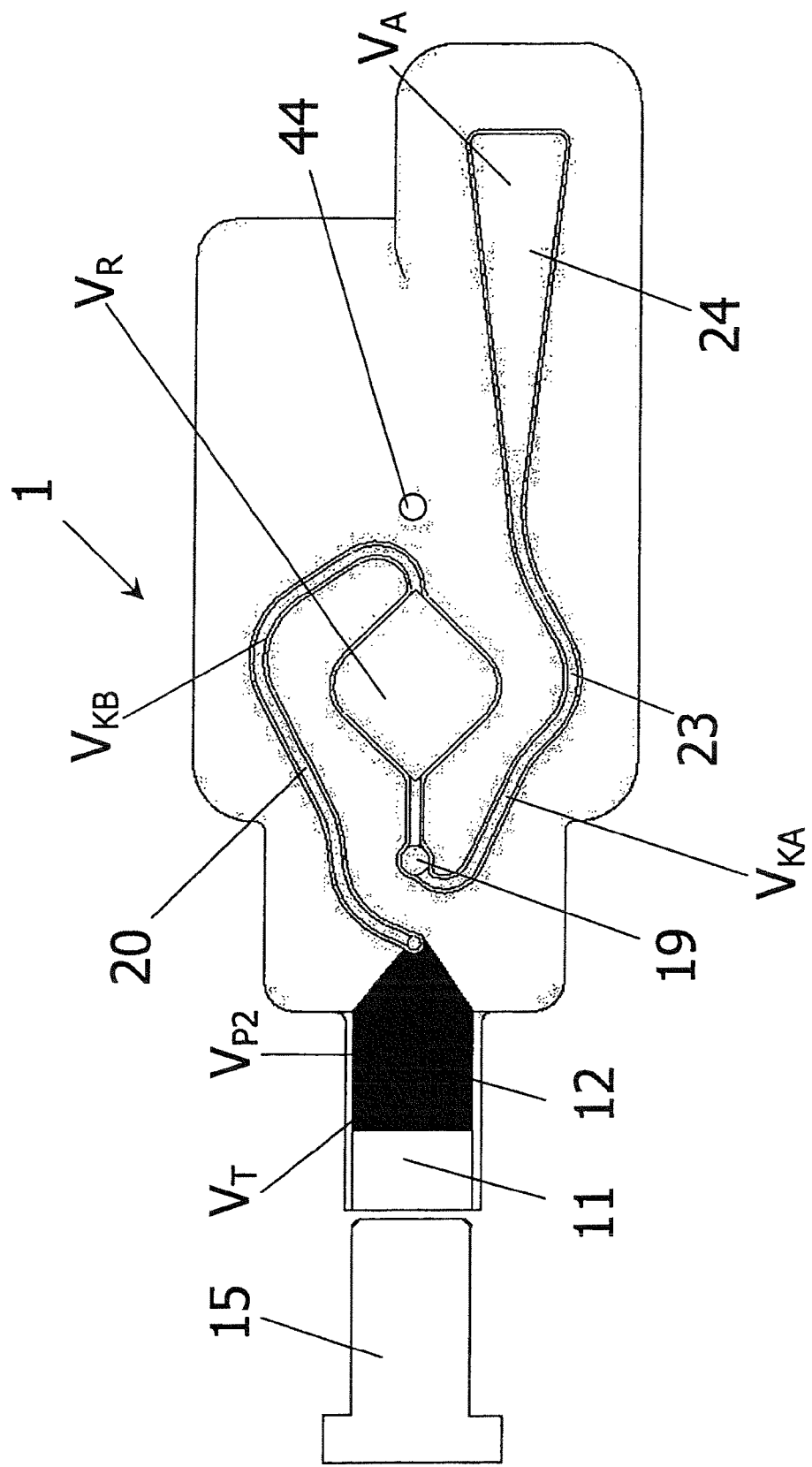
Figure 6:
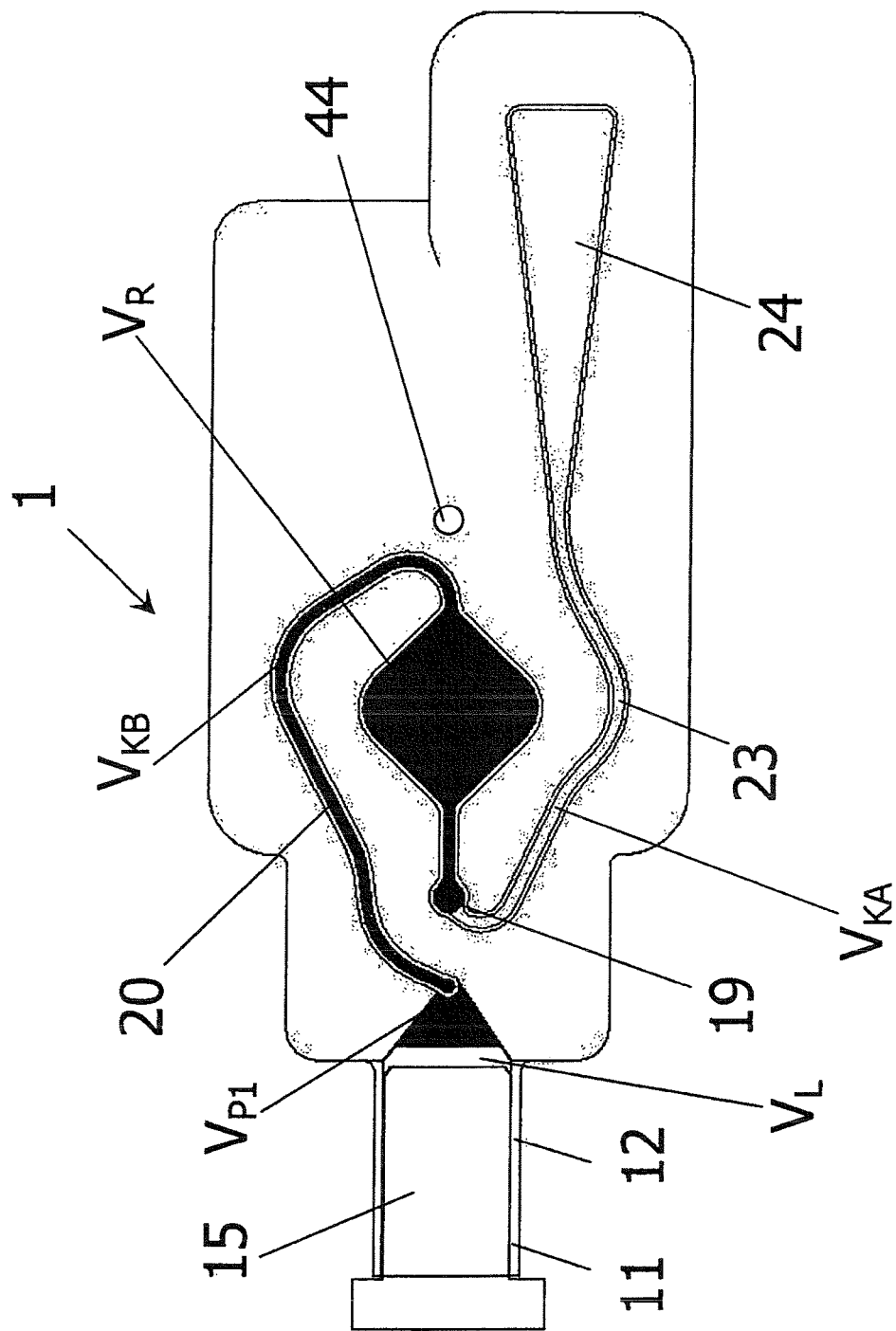
Figure 7:
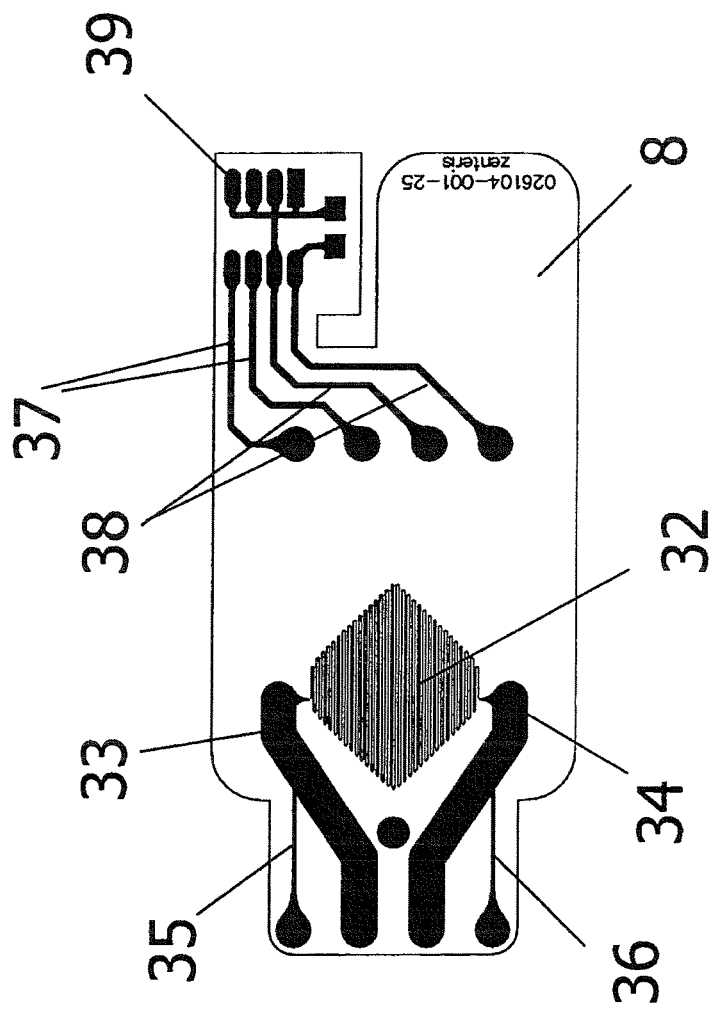
Figure 8:
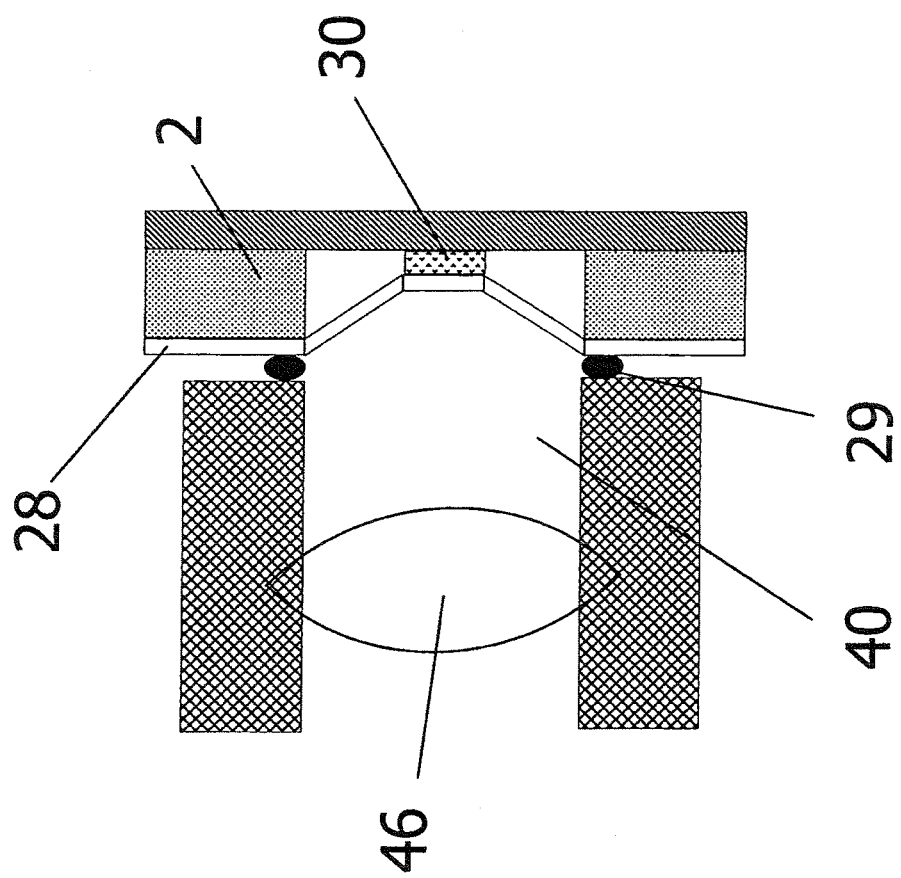
Figure 9:
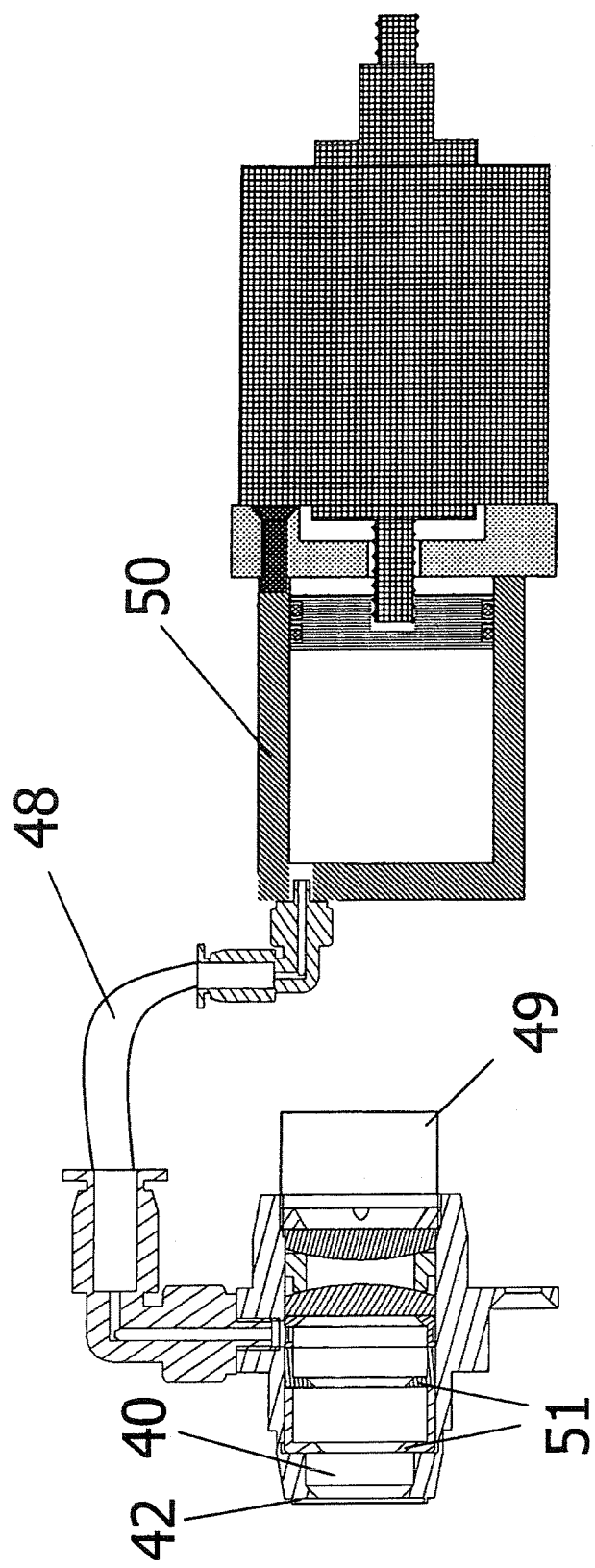
Figure 10:
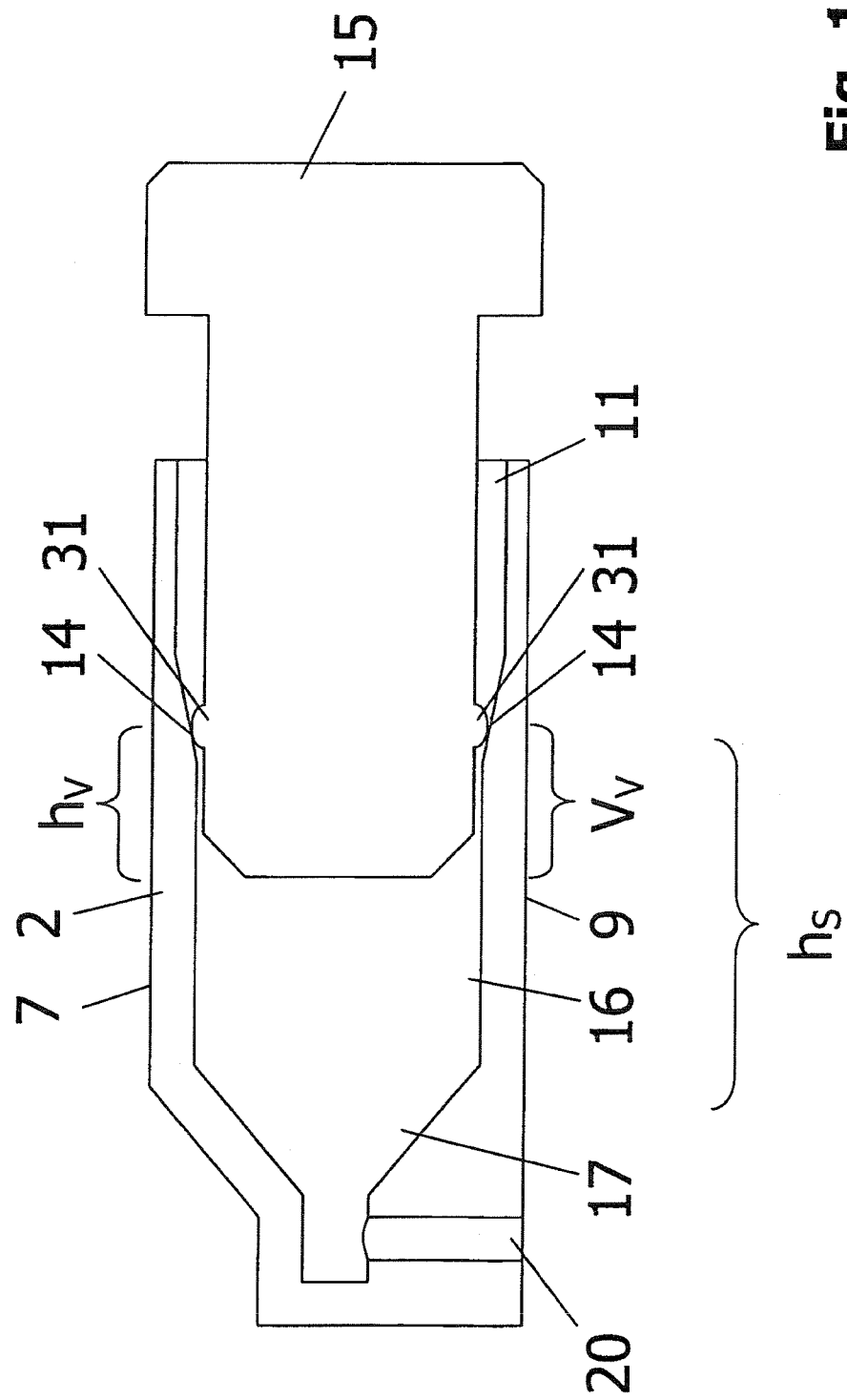

FIG. 2 a view of the casing of FIG. 1 in a partly-sectioned side view together with a stopper, FIG. 3 a cartridge according to the invention, showing a sectional view corresponding to line A-A plotted on the casing of FIG. 2, FIG. 4 a section through the cartridge and a scanning chamber, FIG. 5 the filling process of the cartridge with the stopper not in place, FIG. 6 the filling process of the cartridge with the stopper pressed in, FIG. 7 a circuit board of the cartridge according to the invention with a heating/measuring structure, FIG. 8 a schematic section through the reaction chamber and the scanning chamber, with a film fitting up against a biochip, FIG. 9 a sectional view of the scanning chamber of FIG. 4 and a compressed air supply source connected to it, and FIG. 10 a section through the stopper and a filling nozzle of the cartridge.

A cartridge 1 with a biochip 30 will be described with the aid of FIGS. 1-4.

The cartridge 1 has an elongated roughly bowl- or trough-like casing 2 made e.g. of plastic by injection moulding. The casing 2 comprises a base wall 3 and an all-round side wall 4 with two long sides 5 and two end faces 6. The side of the casing 2 on which the side wall 4 is located is designated as the inside 7.

On the side of the base wall 3 facing away from the side walls 4, a circuit board 8 is fixed to the casing 2. This side of the casing 2 is designated as the outside 9.

At one end face 6 of the cartridge 1, a tubular section extending in the axial direction is designated as the filling nozzle 10. The filling nozzle 10 is formed integrally as one piece with the casing 2.

The filling nozzle 10 has a filling section 11 and a compression section 12, with the filling section 11 located adjacent to the free edge of the filling nozzle 10 and the compression section 12 situated between the filling section 11 and the rest of the body of the cartridge 1 (FIG. 2).

The filling section 11 has a greater clear width than the compression section 12. Provided as a transition between the filling section 11 and the compression section 12 is a chamfer 13. This chamfered section 12 has, roughly in the middle, a sealing point 14, from which point a stopper 15 tightly seals the filling nozzle 10 (FIG. 3).

The compression section 12 is a cylindrical section 16 with circular cross-section, which merges into a funnel-shaped section 17, at the end of which is a filling hole 18. The filling hole 18 is connected to a reaction chamber 22 via a filling line section 20.

A filling indicator may be provided in the cylindrical section 16 of the compression section 12. The filling indicator 19 may be in the form of a marking or calibration mark applied to the inside or outside of the filling nozzle 10. It is also possible to provide a viewing panel or other suitable means in the filling nozzle 10, for use in checking the sample quantity inserted in the filling nozzle 10.

From the filling hole 18, the filling line section 20 extends roughly perpendicular to and through the base wall 3. At the outside 9 of the base wall 3, the filling line section 20 is in the form of a half-open recess, wherein the open side is bounded by the circuit board 8.

Provided roughly in the centre of the base wall 3 is a rhomboid-shaped through hole 21 which bounds the reaction chamber 22.

One tip of the rhomboid-shaped through hole 21 points in the direction of the filling nozzle 10 and an opposite tip of the rhomboid-shaped through hole 21 points away from the filling nozzle 10.

The filling line section 20 extends around the rhomboid-shaped through hole 21 and leads into the tip of the rhomboid-shaped through hole 21 which faces away from the filling nozzle 10.

Connected to the tip of the rhomboid through hole 21 oriented in the direction of the filling nozzle 10 is a compensation line section 23. The compensation line section 23 is formed in the outside 9 of the base wall 3 as a half-open recess, which in turn is bounded by the circuit board 8. The compensation line section 23 extends on the side of the rhomboid through hole 21 opposite the filling line section 20 around the through hole 21 and leads into one tip of a half-cone-shaped compensation chamber 24.

The half-cone-shaped compensation chamber 24 is in the form of a recess, open on one side, on the underside 9 of the base wall 3. A half-cone-shaped section of the base wall 3 arches over the circuit board 8 and bounds the compensation chamber 24, which extends to around the height of the side walls 4.

Provided in the compensation line section 23, adjacent to the tip of the rhomboidal through hole 21, is a circular recess. The recess is closed on the inside 7 of the base wall 3 by a transparent hemisphere 26 moulded integrally to the base wall 3. Adjacent to the hemisphere 26 is a polished cone 25, extending into the compensation line section 23. The tip of the cone 25 points towards the circuit board 8 and has an angle of 90°. The plastic material of the casing 2 is transparent and preferably translucent. The hemisphere 26 forms a lens and is preferably polished on its surface. The hemisphere 26 and the cone 25 form a filling indicator 27 for the reaction chamber 22.

If the filling indicator 27 is not filled with sample solution then the hemisphere 26, owing to the total reflection of the incident light, has a light colour. If the filling indicator 27 is filled with sample fluid, then the cone 25 is surrounded by sample fluid, so that the total reflection is attenuated. This causes the circuit board 8 located beneath to become visible, and the filling indicator appears dark.

On the inside 7 of the base wall 3, the reaction chamber 22 and the through hole 21 respectively are bounded by a flexible transparent film 28. The film 28 is affixed to the base wall 3. The 28 has a thickness of around 127 µm. The film 28 is made preferably from a fluorinated ethylene-propylene copolymer (e.g. FEP) or another suitable plastic. The clearance from the circuit board 8 comes to around 0.9 mm, corresponding roughly to the thickness of the base wall 3. The flexible transparent film 28 serves as a window for the optical measurements of the sample solution.

A continuous seal 29 is provided on the film 28 in the area around the through hole 21.

In the area of the rhomboidal through hole 21 and the reaction chamber 22, the circuit board 8 forms a boundary wall of the same. In the area of the filling line section 20, the compensation line section 23, the filling indicator 27 and the compensation chamber 24, the circuit board 8 seals tightly with these recesses in such a way that they are bounded at the bottom and form a continuous, communicating and self-contained passage structure.

The circuit board 8 contains contact faces, a digital storage medium (e.g. an EEPROM) and an internal heating/measuring structure 32, which will be explained in detail below. Instead of the circuit board 8, it is also possible to provide for heating and cooling a plate of a material with good thermal conductivity, such as e.g. aluminium or copper. This plate can then be tempered from the outside using a heating/cooling device.

In roughly the centre of the through recess, a biochip 30 is mounted on the circuit board 8. The biochip has an active side, on which probes are immobilised at predetermined spots. The active side of the biochip faces towards the film 28. The biochip 30 has a height of around 0.7 mm and a number of spots=M×N. To avoid optical back reflections and undesired fluorescent radiation from the circuit board 8, the biochip 30 is optically opaque on the reverse and is not fluorescent, e.g. coated with black chrome.

In producing the cartridge 1, firstly the biochip 30 is fixed to the circuit board 8 and then the circuit board 8 is bonded to the casing 2. The bond between the circuit board 8 and the biochip 30 is made with an adhesive bonding layer, such as e.g. a suitable adhesive tape (suitable for biological reactions) or else a silicone adhesive.

The circuit board 8 with affixed biochip 30 is then aligned with the casing 2 and fixed to it. A durable, temperature- and water resistant bond may be realised e.g. by using biologically-compatible adhesive tape, silicone adhesive, by laser welding, by ultrasonic welding or by biologically-compatible adhesives.

At the same time it is possible to cover a large area of the circuit board 8 with the adhesive tape (or adhesive), to affix the biochip 30 over the heating/measuring structure, and then to align the casing 2 with the biochip 30 and to fix the circuit board 8 over the whole surface of the casing 2.

A second option for bonding the circuit board 8, biochip 30 and casing 2 lies in the targeted flat bonding of the biochip 30 to the circuit board 8 (adhesive only beneath the biochip 30) and the subsequent fixing of the casing 2, wherein the adhesive layer is provided only outside the reaction chamber 22. With this type of bonding, the transfer of heat from the heating/measuring structure in the circuit board 8 into the reaction chamber 22 is more efficient.

The reaction chamber 22 is bounded between the circuit board 8 and the film 28 and by the edge of the rhomboidal through hole 21. The circuit board 8 is provided with the heating/measuring structure in order to heat up the biochip 30 to a predetermined temperature and to measure the temperature. The film 28 serves as a viewing panel for an optical detection device, which is able through the film 28 to make an optical scan of spots on the biochip 30. Since the 28 is flexible, it may be placed on the surface of the biochip 30 in order to scan it.

To close the filling nozzle 10 and to create the overpressure in the reaction chamber 22, a stopper 15 is provided. The stopper is made preferably of a thermoplastic elastomer (TPE). The stopper 15 is cylindrical with a circular cross-section. The outside diameter of the stopper 15 is such that it may be held virtually without play in the compression section 12 of the filling nozzle 10. The cylindrical compression section 12 of the filling nozzle 10 and the stopper 15 form a kind of cylinder-piston system. The stopper 15 is provided with a seal ring 31 of the same material as and integrally moulded with the stopper. The stopper 15 may also be provided with a continuous groove, in which a seal ring 31 is located. The stopper 15 provides a fluid-tight seal of the hollow spaces of the cartridge 1 after approx. one-third of its length has been inserted into the filling nozzle 10.

On the inside 7 of the casing 2 there are around the reaction chamber 22 three means for guidance, centring and as a stop for a detection device 49.

In the area of the tip of the rhomboidal reaction chamber 22 oriented towards the filling nozzle 10, two opposite sections of the long sides 5 of the side wall 4 are elevated relative to the remainder of the side wall 4. These two sections are designated as stops 45. They are designed for guidance and as stops for a scanning chamber.

In the area of the tip of the reaction chamber 22 oriented towards the compensation chamber 24, a circular centring pin 44 is moulded on at right-angles. The centring pin 44 serves in conjunction with the stops 45 for centring when the scanning chamber 40 is put in place and as a stop for the scanning chamber 40.

The filling and compensation line sections 20, 23 are as short as possible and are designed with the smallest possible cross-section, so that the total volume is kept small and the necessary surplus of sample fluid is as low as possible. The line sections 20, 23 are however guided around the reaction chamber 22, so that in filling, in which the filling nozzle 10 is arranged at the top, the reaction chamber 22 fills from the bottom. This ensures that the reaction chamber 22 is filled without creation of bubbles. In operation, the filling nozzle 10 is at the bottom and the compensation chamber 24 at the top, so that sample fluid may be displaced reversibly into the compensation chamber 24, while the air bubble during displacement is always above the sample fluid in the compensation chamber 24.

The process of a temperature-controlled biological detection reaction requires the setting of precise temperatures of the sample fluid in the reaction chamber. Here, in the course of a PCR, temperatures of e.g. between 30° C. and 98° C. are selected. The temperature distribution of the sample fluid should be homogeneous in the reaction chamber and temperature changes (heating, cooling) should be made quickly.

Provided on the circuit board 8 (FIG. 7) is a heating/measuring structure 32, which with current passed through the ohmic resistor acts as a heater. With this, the sample fluid in the reaction chamber 22 is heated to the required temperature T. The heating/measuring structure 32 may at the same time be used as a temperature detector, by using the resistance characteristic R(T) to determine temperature.

A preferred embodiment of the layout of the circuit board 8 is shown in FIG. 7. The meandering heating/measuring structure 32 is formed by a thin conductor path with a width of 60 μm and a thickness of 16 μm. It is around 480 mm long. At room temperature it has an electrical resistance of around 6 to 8 ohms. The conductor path is made of copper, preferably copper with a purity of 99.99%. Copper of this level of purity has a thermal coefficient which, in the temperature range relevant here, is virtually constant. In its totality the heating/measuring structure 32 forms a rhombus with an edge length of approximately 9 mm. Conductor paths already exist which have a copper layer with a thickness of 5 μm and on which structures with a width of 30 μm are formed. A resistance of approximately 100 ohms to 120 ohms has been obtained with conductor paths of this kind.

The biochip 30 has an edge length of only 3 mm, meaning that the rhombus formed by the heating/measuring structure 32 and a temperature homogenisation layer covers a greater area than the biochip 30.

The circuit board 8 may be provided with a temperature homogenisation layer, which effects homogenisation of the temperature distribution on the upper side of the circuit board 8. The temperature homogenisation layer is a copper layer which is nickel-plated and provided with an additional gold layer. The gold layer has the advantage that it is inert for biological materials and therefore biological materials may come into direct contact with this layer in the reaction chamber. This reaction chamber 22 may therefore also be used for other experiments besides those involving the biochip. This homogenisation layer has good thermal conductivity. Instead of a combined copper-nickel-gold layer, a relatively thick copper layer could also be provided.

A heating conductor path integrated in the circuit board 8 has a low inherent thermal capacity. This makes it possible to achieve high rates of heating of the sample fluid in the reaction chamber 22.

The end points of the meandering heating/measuring structure 32 merge in each case into a very wide conductor path 33 and 34, which serve to supply the heating current and themselves have only a low resistance due to their considerable width. In addition, there is in each case a further conductor path 35 and 36 connected to these two conductor paths 33 and 34 in the area of the connection point of the meandering heating/measuring structure.

These two additional conductor paths 35 and 36 are used to pick up the voltage drop at the heating/measuring structure 32. The electrical control of the heating/measuring structure 32 is described in detail in WO 2008/064865 A2. Reference is made to this document in respect of the control of the heating/measuring structure 32.

The circuit board 8 has conductor paths 37 and corresponding contact points 38, 39 for the connection of an electrical semiconductor memory. This semiconductor memory is used to store calibration data for the heating device and also the data from the biological experiments to be made with the biochip of the cartridge. This data is therefore stored with no risk of confusion.

The dimensioning of the filling nozzle 10, the filling line section 20, the reaction chamber 22, the compensation line section 23, the compensation chamber 24 and the stopper 15 of the cartridge 1 according to the invention will be described below with the aid of a typical embodiment (FIG. 5, FIG. 6, FIG. 10).

The volume of the compensation chamber $V_A$ under the assumption that air behaves like an ideal gas, that the pressure build-up is isothermal, and the fluid sample is not compressible, is given by $$V_A = \frac{p_0}{p_1 - p_0}(V_{KB} + V_R) - V_{KA},$$

wherein $V_{KB}$ is the volume of the filling line section 20 (6.5 μl), $V_{KA}$ the volume of the compensation line section 23 (... μl), $V_R$ the volume of the reaction chamber 22 (35.4 μl+8 μl), $p_0$ the environmental pressure (1 bar) and $p_1$ the increased pressure (1.4 bar).

To begin with, In calculating the height of the stopper 15 penetrating into the compression section 12 a first penetration volume of the stopper $V_V$ is calculated, which should penetrate into the compression section 12 of the filling nozzle 10 without the filling nozzle 10 being sealed. This is therefore the volume which penetrates into the compression section 12, until the stopper 15 seals with the compression section 12. The first penetration volume of the stopper $V_V$ follows from the overall volume $V_t$ (150.2 μl) of the filling nozzle between the chamfer and the filling hole, less a surplus volume $V_{P1}$ (10 μl) of the sample fluid which should remain in the filling nozzle, so that with movements of fluid no air can gain access to the filling line section 20, a sample volume $V_{P2}$ (49.9 μl), which is comprised of the 35.4 μl referred to above, 6.5 μl for the filling line section 20 and 8 μl for compensation for the bulging of the film 28, and an air reserve $V_L$ of 30 μl in the 10 for any excess pipetted sample:

$$V_V = V_t - V_{P1} - V_{P2} - V_L$$

The air reserve $V_L$ remains trapped between the sample solution and the stopper 15. The first penetration depth $h_V$ of the stopper 15 in the compression section 12 therefore follows from the penetration volume $V_V$ divided by the cross-sectional area of the stopper $A_V$:

$$h_V = \frac{V_V}{A_V}$$

A second penetration depth $h_S$ specifies how far the stopper 15 must penetrate into the compression section 12 after sealing, so that the increase of pressure to 1.4 bar is effected. Since the sample volume $V_{P2}$ (49.9 μl) is to be completely displaced from the filling nozzle 10, all that remains in the filling nozzle 10 after the stopper has been pressed in fully are the surplus volume $V_{P1}$ (10 μl) of the sample fluid and the air reserve $V_L$, which is compressed on account of the pressure build-up. The volume $V_{t'}$ displaced by the stopper 15 after it has been fully pressed in thus follows from the following formula:

$$V_{t'} = V_t - V_{P1} - \frac{p_0}{p_1}V_L$$

The second penetration depth $h_S$ of the stopper 15 in the compression section 12 therefore follows from the second penetration volume $V_{t'}$ divided by the cross-sectional area of the stopper 15 $A_V$:

$$h_S = \frac{V_{I'}}{A_V}$$

The connection of the cartridge 1 to an apparatus for the analysis of biological samples using temperature-controlled biological reactions will be described below.

This apparatus according to the invention comprises a scanning chamber 40, a detection device 49 and a compressed air supply source 50.

The scanning chamber 40 is in the form of a tube. The tube 40 is placed with an open sample side 41 on to the film 28 bounding the reaction chamber 22 or on to the seal 29 provided on top thereof.

The diameter of the tube 40 on the sample side 41 corresponds to the diameter of the seal 29 located on the film 28. The sample side 41 is bounded at the end by a sharp-edged continuous blade 42. The blade 42 is so designed that, when the scanning chamber 40 is placed on the cartridge 1, it penetrates into the seal 29 of the cartridge 1 and provides a pressure-tight connection.

Provided on the sample side 41 of the tube 40 are recesses 43 to accommodate the centring pin 44 and the two stops 45 of the cartridge 1. By means of the stops 45 and the centring pin 44, the tube 40 is positioned exactly on the cartridge 1 and its seal 29 respectively and over the reaction chamber 22. The stops 45 set the exact contact pressure with which the scanning chamber 40 rests pressure-tight on top of the cartridge 1.

Located at the end of the scanning chamber 40 opposite the sample side 41 is part of an optical system 46. In the present embodiment e.g. two lenses 47 are provided.

Connected at around the middle of the tube 40 is a compressed air line 48, in turn connected to a compressed air supply source 50. The compressed air supply source 50 is so designed as a cylinder/piston unit with an electrically controlled linear drive, that the pressure at the piston may be set precisely through the linear drive. Over the compressed air supply source 50 and the compressed air line 48, the scanning chamber 40 may be pressure-loaded by compressed air in the area between the lenses 47 and the cartridge 1. By this means the film 28 is applied flat to the biochip 30.

Located behind the two lenses 47 is a detection device 49 for scanning the biochip 30.

In the present embodiment, three apertures 51 are provided in the scanning chamber 40.

The detection device 49 for readout of the biochip 30 is described in detail in WO 2007/135 091 A2, to which reference is hereby made. The detection device 49 comprises an LED with cast-on plastic optics, LED optics, illumination optics, an exciting filter, a dichroic mirror, an NA aperture, an emission filter, readout optics and a camera.

Preferably used as light source is a single high-performance LED with high optical power density and LED optics with high numerical aperture (NA). High-performance light-emitting diodes are light-emitting diodes with a luminous flux of at least 35 lm. Preferably light-emitting diodes with a luminous flux of at least 40 lm, at least 50 lm or at least 100 lm are used. In the present embodiment the light-emitting diode Luxeon Star (red, 3 W electrical power consumption, 90 lm luminous flux) is used.

The light-emitting diodes used emit roughly punctuatedly light. By this we mean light-emitting diodes with an emitting surface not greater than 1 mm×1 mm. Preferably the emitting surface does not exceed 0.5 mm×0.5 mm. The smaller the emitting surface, the better the light may be concentrated, with the individual light rays of the light ray concentration aligned parallel to one another.

One advantage of an LED for the illumination of biochips also lies in the variability of the wavelength. LEDs are available in the whole visible spectrum with high efficiency. A further benefit of LEDs e.g. compared with lasers, for flat illumination, is that no intensity modulations due to coherence occur at the surface.

For the typical dyes to be detected in the spots on the biochip, a spectrally well adjusted LED may be used as light source.

For example:
 dye Cy5 absorption maximum at 649 nm
  excitation by LED LUXEON LD3 (colour red, max. at 630 nm)
 dye Cy3 absorption maximum at 514 nm
  excitation by LED LUXEON LM3 (colour green, max. at 530 nm)
 dye Alexa Fluor 532 absorption maximum at 532
  excitation by LED LUXEON LM3 (colour green, max. at 530 nm)

The choice of an LED is made for a wavelength range $\Delta\lambda_E$ which is required for fluorescence measurements (e.g. for dyes Cy5, Cy3, Alexa, . . . ). LEDs are small and compact with high efficiency and a long life expectancy.

The camera has a flat CCD element as detector, so that a rectangular, in particular square image may be recorded. The camera is so designed that exposure times of more than 20 seconds are possible in its use. Normally the maximum exposure time with such cameras is limited to a few seconds. As a rule the camera is exposed for 5 to 10 seconds to record the image of the biochip. The longer the exposure time, the weaker the fluorescence signals which can be detected. The strength of the fluorescence signals depends heavily on the number of PCR cycles performed on the biochip. An individual FOR cycle lasts for around half to several minutes. By means of long exposure times, which may be extended by quite a few seconds, a processing time of several minutes can be saved in the extent of the PCR cycles, and the overall processing time may be kept short. These relatively long exposure times also represent an advantage compared with conventional scanners, which scan the individual spots in sequence, since with this procedure the exposure time is not freely variable.

Through the dichroic mirror, the illumination optics are separated from the readout optics. The illumination optics are provided with a high numerical aperture. The readout aperture is located in the beam path of the readout optics. This aperture reduces the numerical aperture of the readout optics, by means of which a contrast-rich image with minimal imaging errors of the spots of the biochip is obtained on the camera. The numerical aperture of the readout channel should not exceed 0.25 and should preferably be no greater than 0.15.

The two lenses 47 in the tube 40 are parts of both the illumination channel and also the readout channel.

The use of the apparatus for analysing biological samples using temperature-controlled biological reactions is described below (FIG. 8, FIG. 9).

The scanning chamber 40 is placed with its sample side 41 on the film of the cartridge 1. In the course of this, the recesses 43 of the scanning chamber 40 engage in the centring pin 44 and the two stops 45, by which means the scanning chamber 40 is positioned and the contact pressure on the seal 29 is limited. At the same time the blade 42 penetrates into the seal 29 and ensures a pressure-tight connection.

The scanning chamber 40 is filled with air through the compressed air line. In this way an overpressure of between 2 and 4 bar is produced in the space sealed between the optics and the transparent film 28. Due to the overpressure, the transparent film 28 fits up against the biochip 30 and displaces the fluorescence excess of the sample fluid over the biochip 30.

The fluorescence in the rest of the sample chamber is screened off. It is therefore possible to make a fluorescence image of the biochip 30.

A mixing (forced convection) of the sample has a positive effect on the speed of reaction of the hybridisation/incubation, therefore the hybridisation/incubation time reduces and higher signal intensities are possible. Such forced convection may be obtained by varying the overpressure at the outside of the film.

Due to the internal overpressure of the cartridge 1 amounting to 0.4 bar, the "window" film 28 is mechanically stressed, in particular during heating-up, and would be subject to plastic deformation. This stress may be neutralised by an external overpressure, also amounting to 0.4 bar. This is of advantage e.g. during amplification, in which the film is subject to considerable thermal stress.

In the case of the apparatus according to the invention it is advantageous that extensive surface irregularities on the biochip 30, other than with rigid cover glass slides known from the prior art, have no effect on the fluorescence signal.

On account of its lower thickness and the closeness of the film 28 to the biochip 30, the optical quality of the film 28 has only slight effect on the ability to evaluate the fluorescence signals.

The application of the film 28 to the biochip 30 is reversible, so that real-time PCR is possible.

In the cartridge or in the apparatus, a cooling device for cooling the reaction chamber 22 may also be provided.

In principle it is possible within the scope of the present invention for the filling nozzle and stopper also to be used in conjunction with a cartridge, in which a flexible electrical circuit board is provided, wherein the viewing window may be rigid, e.g. in the form of a glass panel.

| | List of reference numbers: |
|---|---|
| 1 | cartridge |
| 2 | casing |
| 3 | base wall |
| 4 | side wall |
| 5 | long side |
| 6 | end face |
| 7 | inside |
| 8 | circuit board |
| 9 | outside |
| 10 | filling nozzle |
| 11 | filling section |
| 12 | compression section |
| 13 | chamfer |
| 14 | sealing point |
| 15 | stopper |
| 16 | cylindrical section |
| 17 | funnel-shaped section |
| 18 | filling hole |
| 19 | filling indicator |
| 20 | filling line section |
| 21 | through hole |
| 22 | reaction chamber |
| 23 | compensation line section |
| 24 | compensation chamber |
| 25 | cone |
| 26 | hemisphere |
| 27 | filling indicator |
| 28 | film |
| 29 | seal |

| | List of reference numbers: |
|---|---|
| 30 | biochip |
| 31 | seal ring |
| 32 | heating/measuring structure |
| 33 | conductor path (heating current) |
| 34 | conductor path (heating current) |
| 35 | conductor path (measuring current) |
| 36 | conductor path (measuring current) |
| 37 | conductor path |
| 38 | contact point |
| 39 | contact point |
| 40 | scanning chamber |
| 41 | sample side |
| 42 | blade |
| 43 | recess |
| 44 | centring pin |
| 45 | stop |
| 46 | optics |
| 47 | lens |
| 48 | compressed air line |
| 49 | detection device |
| 50 | compressed air supply source |
| 51 | aperture |

The invention claimed is:

1. A cartridge for analyzing biological samples, comprising:
a reaction chamber and a biochip mounted in the reaction chamber,
a filling nozzle connected so as to communicate with the reaction chamber, and
a compensation chamber connected so as to communicate with the reaction chamber,
a compensation line section and a filling line section communicating among the reaction chamber, a filling level indicator and the compensation chamber such that before filling, normal pressure exists within the compensation line section, the filling line section, the reaction chamber, the filling nozzle and the compensation chamber of the cartridge,
wherein the reaction chamber, the compensation chamber and the said line sections are sealed,
wherein the filling nozzle forms a free passage to the reaction chamber from outside the cartridge, and a stopper is provided which fits positively and tightly in the filling nozzle such that, when pressed in over a certain distance, fluid is displaced from the filling nozzle towards the reaction chamber
wherein the filling nozzle has a filling section, which allows the biological sample to be introduced from outside, and which leads into a cylindrical compression section, wherein the filling section has a larger cross-section than the compression section and the compression section is connected to the reaction chamber via the free passage, and the stopper is designed so that it is held tightly in the compression section, wherein the reaction chamber is bounded on an upper side by a transparent, flexible film, which forms a viewing window.

2. The cartridge according to claim 1, wherein the volume of the compensation chamber, the reaction chamber and said lines communicating therewith including the filling nozzle and the volume displaced by the filling nozzle are so dimensioned that, with a sample of predetermined volume in the reaction chamber, an increase in pressure of at least 0.2 bar is generated.

3. The cartridge according to claim 1, wherein the filling nozzle is connected to the reaction chamber via a filling hole, with a diameter designed so that, on filling without pressure increase, no sample fluid passes through the filling hole due to its surface tension.

4. The cartridge according to claim 1, wherein the stopper is provided with a continuous seal ring, which is designed such that it makes a fluid-tight seal with the compression section.

5. The cartridge according to claim 1, wherein a seal which surrounds the viewing window is provided for pressure-tight placing on the cartridge of a scanning chamber of an apparatus for the analysis of biological samples.

6. The cartridge according to claim 1, wherein the cartridge has a casing with a through hole to form the reaction chamber, wherein the casing is connected to a circuit board in such a way that the circuit board covers the through hole to bound the reaction chamber, wherein a viewing panel is formed in the side of the reaction chamber opposite the circuit board and a heating/measuring structure is integrated in the circuit board.

7. The cartridge according to claim 1, wherein a the filling line section extends from the filling nozzle around the reaction chamber and leading into an edge area of the reaction chamber at a distance from the filling nozzle.

8. The cartridge according to claim 7, wherein the reaction chamber is connected at its edge area to a filling indicator which lies diametrically opposite the edge area, which is connected to the filling line section.

9. An apparatus for the analysis of biological samples using temperature-controlled biological reactions, the apparatus comprising:
   the cartridge of claim 1, wherein the biochip has an active side and the area of the cartridge opposite the active side of the biochip is in the form of a transparent film and is arranged with clearance from the biochip,
   a detection device, and
   a scanning chamber which is connected to the cartridge in a pressure-tight fashion, in the area of the film, wherein the detection device is connected to the chamber such that the biochip can be scanned through the film and a compressed air line leads into the scanning chamber, so that the film may be so pressurized by air pressure that it is pressed flat against the biochip.

10. The apparatus according to claim 9, wherein a piston/cylinder pump is provided as compressed air supply to pressurize the scanning chamber.

11. An apparatus for the analysis of biological samples using temperature-controlled biological reactions, the apparatus comprising:
   the cartridge of claim 2, wherein the biochip has an active side and the area of the cartridge opposite the active side of the biochip is in the form of a transparent film and is arranged with clearance from the biochip,
   a detection device, and
   a scanning chamber connected to the cartridge in a pressure-tight fashion, in the area of the film, wherein the detection device is connected to the chamber such that the biochip is scanned through the film and a compressed air line leads into the scanning chamber, so that the film is so pressurized by air pressure that it is pressed flat against the biochip.

12. An apparatus for the analysis of biological samples using temperature-controlled biological reactions, the apparatus comprising:
   the cartridge of claim 3, wherein the biochip has an active side and the area of the cartridge opposite the active side of the biochip is in the form of a transparent film and is arranged with clearance from the biochip,
   a detection device, and
   a scanning chamber connected to the cartridge in a pressure-tight fashion, in the area of the film, wherein the detection device is connected to the chamber such that the biochip is scanned through the film and a compressed air line leads into the scanning chamber, so that the film is so pressurized by air pressure that it is pressed flat against the biochip.

* * * * *